United States Patent
Coppi

(10) Patent No.: US 10,065,024 B2
(45) Date of Patent: Sep. 4, 2018

(54) GUIDE-WIRE KIT AND ASSEMBLY, USE AND MOUNTING METHODS

(71) Applicant: Gioachino Coppi, Modena (IT)

(72) Inventor: Gioachino Coppi, Modena (IT)

( * ) Notice: Subject to any disclaimer, the term of this patent is extended or adjusted under 35 U.S.C. 154(b) by 0 days.

(21) Appl. No.: 14/784,398

(22) PCT Filed: Mar. 31, 2014

(86) PCT No.: PCT/IB2014/060324
§ 371 (c)(1),
(2) Date: Oct. 14, 2015

(87) PCT Pub. No.: WO2014/170779
PCT Pub. Date: Oct. 23, 2014

(65) Prior Publication Data
US 2016/0058979 A1 Mar. 3, 2016

(30) Foreign Application Priority Data

Apr. 18, 2013 (IT) .............................. BS2013A0057

(51) Int. Cl.
*A61M 25/09* (2006.01)
(52) U.S. Cl.
CPC ............... *A61M 25/09041* (2013.01); *A61M 2025/09116* (2013.01); *A61M 2025/09125* (2013.01)
(58) Field of Classification Search
CPC ......... A61M 2025/09116; A61M 2025/09125; A61M 25/0113; A61M 25/09041; A61M 25/0905
See application file for complete search history.

(56) References Cited

U.S. PATENT DOCUMENTS 3,537,451 A * 11/1970 Beck .................. A61M 25/0111
604/165.03
4,726,369 A * 2/1988 Mar ................ A61M 25/09041
600/434
(Continued)

FOREIGN PATENT DOCUMENTS

| DE | 19542912 A1 | 5/1997 |
| WO | 2005/072807 A1 | 8/2005 |
| WO | 2006/096262 A2 | 9/2006 |

OTHER PUBLICATIONS

PCT International Search Report and the Written Opinion, Application No. PCT/IB2014/060324 filed Mar. 31, 2014, dated Jun. 25, 2014.

*Primary Examiner* — David J McCrosky
(74) *Attorney, Agent, or Firm* — MacMillan, Sobanski & Todd, LLC

(57) ABSTRACT

Described herein is an assembly having a guide-wire having distally a flexible tip, and a guide-wire kit having comprising an introduction element of the guide-wire, a torque body, proximal to the introduction element, which includes blocking element of the guide-wire to the body, and a slide control which defines a support surface for the guide-wire, manually accessible to control (roto-)translations of the guide-wire, thereby orientations and/or sliding of the flexible tip, when the blocking element is in a release configuration. The torque body, the introduction element and the slide control are each disengageable, independently of the others, from the guide-wire in a radial direction.

13 Claims, 4 Drawing Sheets

(56) References Cited

U.S. PATENT DOCUMENTS

| | | | | |
|---|---|---|---|---|
| 5,312,338 A * | 5/1994 | Nelson | ................... | A61B 17/22 |
| | | | | 600/434 |
| 6,059,484 A | 5/2000 | Greive | | |
| 6,949,104 B2 * | 9/2005 | Griffis | ................... | A61M 25/09 |
| | | | | 600/434 |
| 7,857,770 B2 * | 12/2010 | Raulerson | ......... | A61M 25/0105 |
| | | | | 600/585 |
| 8,114,031 B2 * | 2/2012 | Marsman | ........ | A61M 25/09041 |
| | | | | 600/585 |
| 9,352,130 B2 * | 5/2016 | Moger | ................... | A61M 25/09 |
| 9,597,152 B2 * | 3/2017 | Schaeffer | ............. | A61B 17/221 |
| 2001/0016712 A1 * | 8/2001 | Hamilton | ........... | A61M 25/0113 |
| | | | | 604/170.01 |
| 2003/0036712 A1 | 2/2003 | Heh et al. | | |
| 2005/0245847 A1 | 11/2005 | Schaeffer | | |
| 2006/0146010 A1 * | 7/2006 | Schneider | ......... | A61M 25/0105 |
| | | | | 345/156 |
| 2007/0161969 A1 * | 7/2007 | Andersen | ............. | A61M 25/00 |
| | | | | 604/533 |

\* cited by examiner

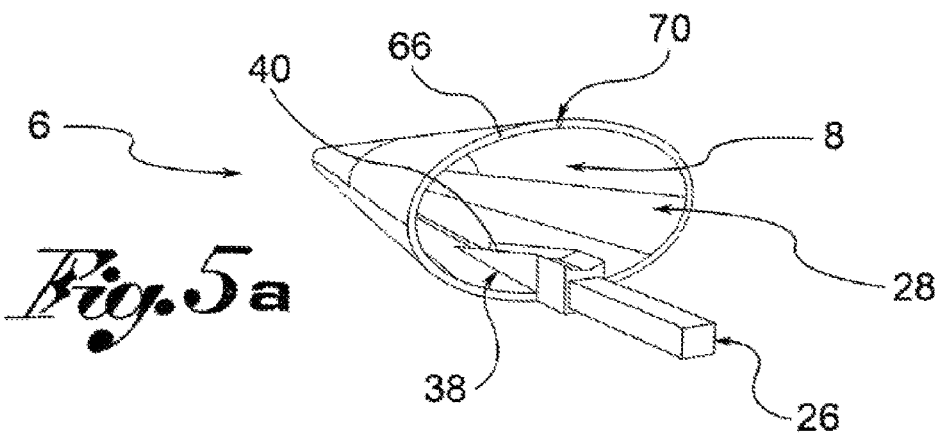
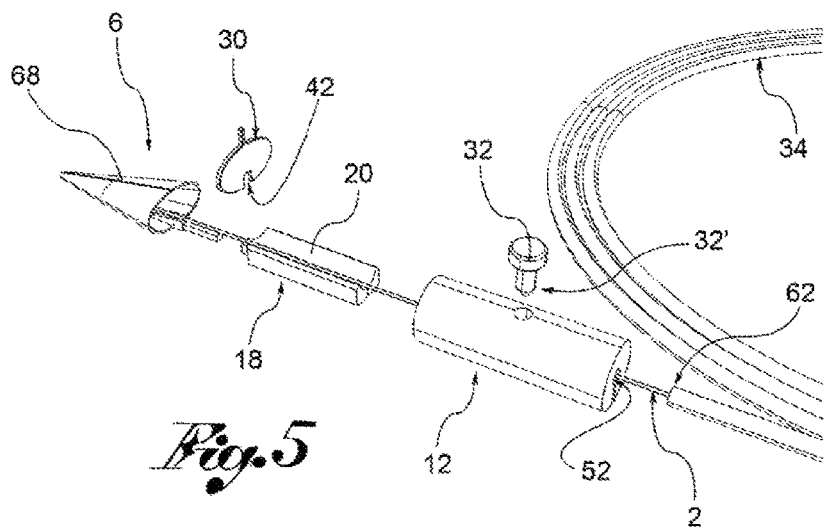
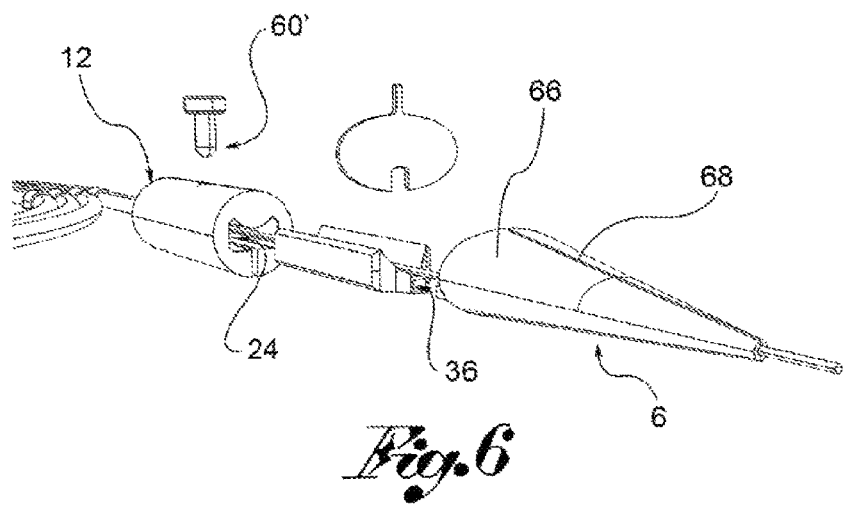

GUIDE-WIRE KIT AND ASSEMBLY, USE AND MOUNTING METHODS

CROSS-REFERENCE TO RELATED APPLICATIONS

This is a national stage application filed under 35 U.S.C. § 371 of international application PCT/IB2014/060324, filed under the authority of the Patent Cooperation Treaty on Mar. 31, 2014, published; which claims the benefit of Patent Application No. BS2013A000057, filed on Apr. 18, 2013. The entire disclosures of all the aforementioned applications are expressly incorporated herein by reference for all purposes.

FIELD OF INVENTION

The present invention concerns a guide-wire kit, and an assembly comprising such kit.

SUMMARY

In the medical field, and above all in angiology, the use of mini invasive procedures is increasingly more widespread, for intervening surgically on patients: such procedures are performed by entering the patient's vessels at a point of easy access (nearly always the femoral artery of the groin) and reaching the desired area of intervention following the tortuous and branched path of the blood vessels.

To do this, filiform guides and catheters are used specific to the medical procedure and to the anatomic area being operated on. For example, such catheters can be equipped with expandable balloons to position a stent, or to widen a stenosis of a blood vessel.

In any case, whatever the procedure to be performed, the first operation is to apply a so-called introduction catheter (or access catheter): using a needle, the skin of an easy-to-reach artery is perforated and, through such needle, is made to transit the filiform guide, which is pushed high enough in the artery. Once the needle has been removed, along this wire is made to slide the introduction catheter consisting of a proximally valved conduit comprising a tapered spindle having a central channel inside which the previously-fitted filiform guide will run.

After the introduction catheter has been pushed far enough into the vessel, it remains firmly in position and will be used for all the subsequent operations inasmuch as, through the valved conduit, all the endoluminal operating instruments will be made to pass (e.g., special guides, angiographic catheters, operating catheters, stents, balloons, etc.) along the arterial tree.

These operating instruments must, as has been said, be conducted from the access point in the introduction catheter to the operating area, causing them to move forward along special previously-positioned guides, which are rarely the same filiform guide described previously.

In order to first of all reach the operating area, each special guide must perforate the valve of the introduction catheter, and must be able to be manipulated from outside, performing rotary and pushing movements to direct the tip of the guide following the vessel branches.

The precise positioning of the guide and the conduction of the catheter along it are extremely complex operations, which have to be performed very carefully, reducing involuntary movements to the utmost, thereby minimizing any related risks for the patient.

Such operations are in any case made complex by the sterically blocked space in correspondence to the aforementioned access point into the introduction catheter, inasmuch as the catheters used can also be more than one at a time, or because of the fact that articulated operations can produce an alternation of special guides and different catheters in consecutive surgical stages.

It would therefore be desirable for the access area to be easily freeable of the structures meant to position the special guides, and in particular for such disengagement not to result in such structures coming out of the axial extremity of the guides.

SUMMARY OF THE INVENTION

The present invention falls within such context, and proposes to provide an assembly and a kit able to remove and fit the guide-wire positioning and manipulation parts, in such a way as to be able to freely access the access point, and which permit their quick reconnection to the guide-wire in case of renewed necessity.

Such object is achieved by means of an assembly according to the claim 1, by means of a kit, and by means of methods as described herein. The claims dependent on these show advantageous or preferred embodiments.

The object of the present invention will now be described in detail, with the aid of the attached tables.

BRIEF DESCRIPTION OF THE DRAWINGS

FIGS. 4, 5 and 6 show the assembly in the preceding figures in separate parts, so as to evidence the different couplings between the components.

DETAILED DESCRIPTION OF THE INVENTION

Figure 1:
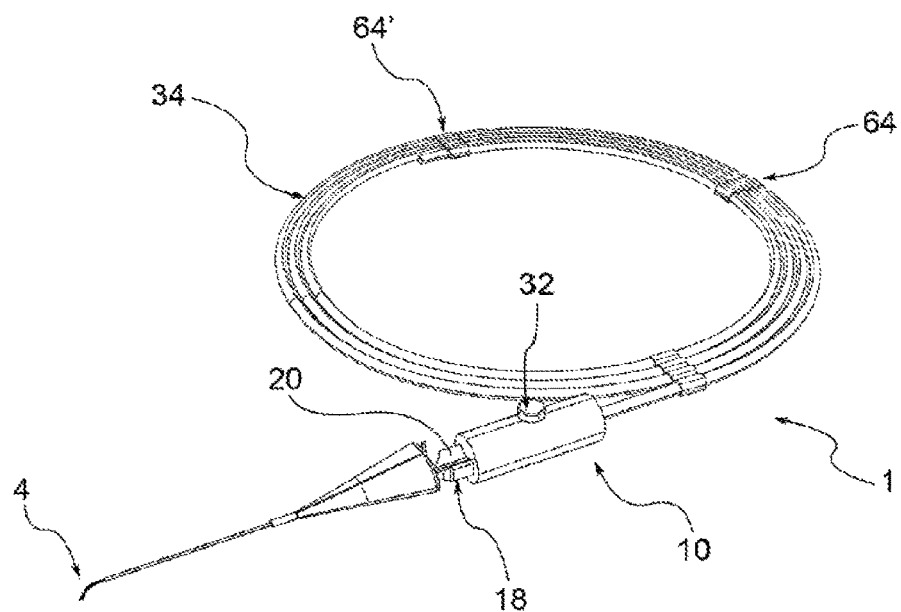
FIGS. 1 and 2 show two perspective views from different angles of an assembly subject of the present invention, in agreement with a possible embodiment.
Figure 2:
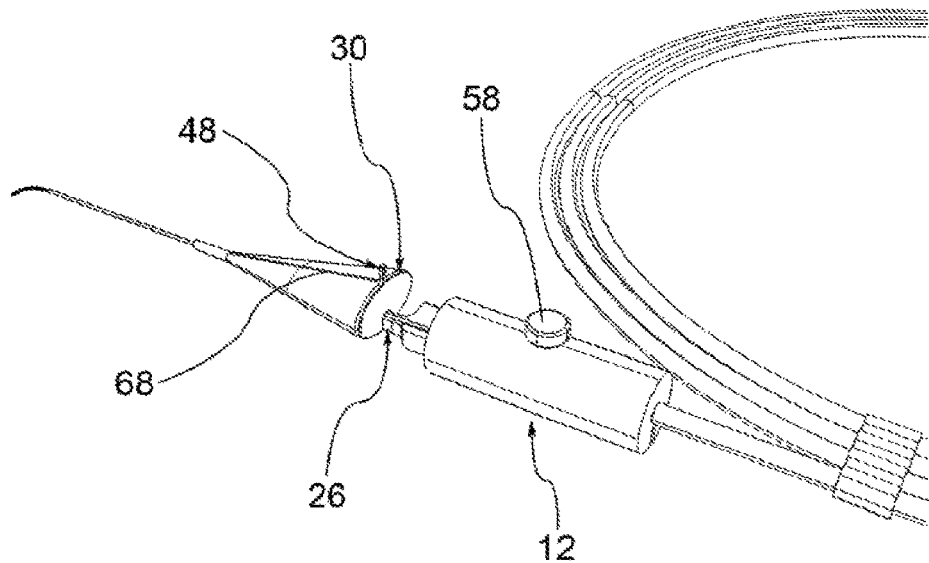
Figure 3:
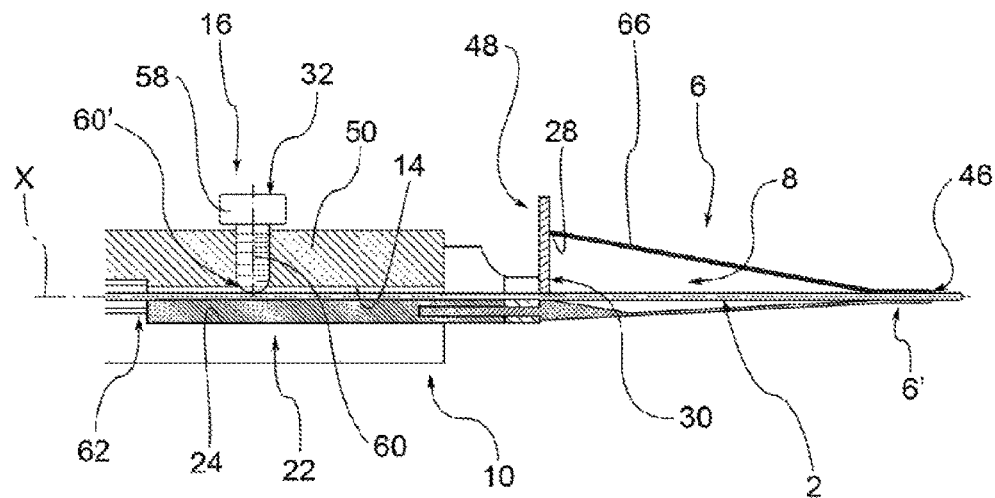
FIG. 3 represents a longitudinal section of the assembly according to the FIG. 1 or 2.
Figure 4:
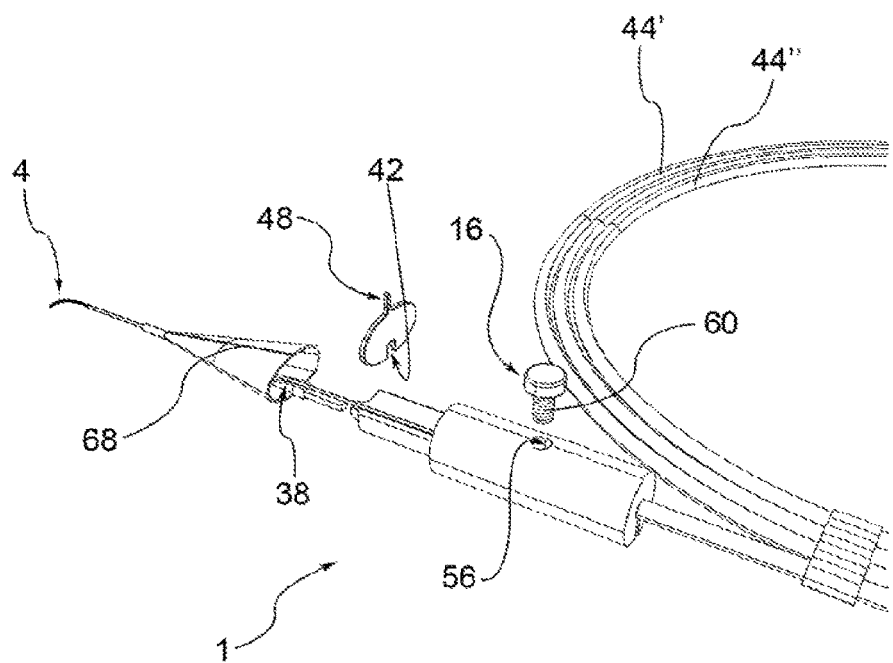
Figure 7:
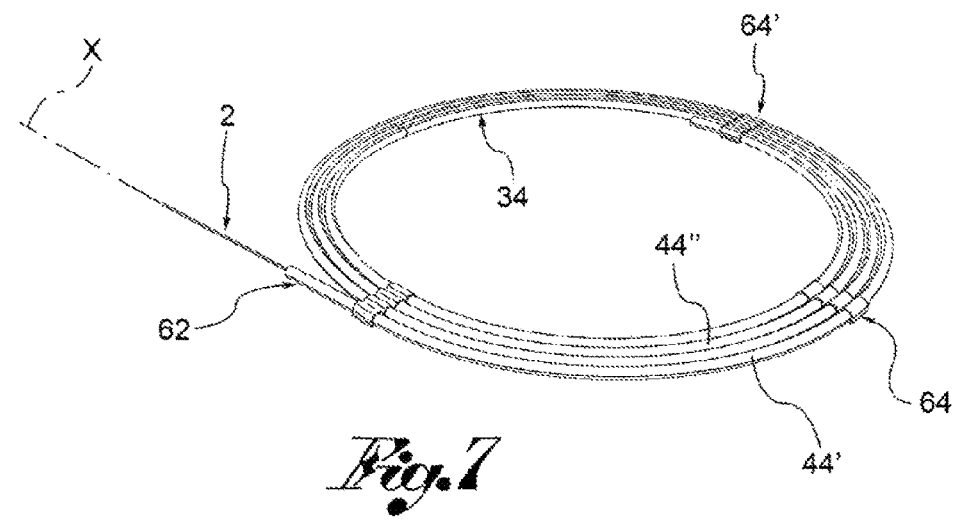
FIGS. 7, 8 and 9a, 9b show perspective views of a guide-wire container respectively with a respective guide wire, a slide control and a torque body (in proximal and distal view) in agreement with possible embodiments, where from the torque body have been deliberately omitted the blocking means of the guide-wire for greater clarity.
Figure 8:
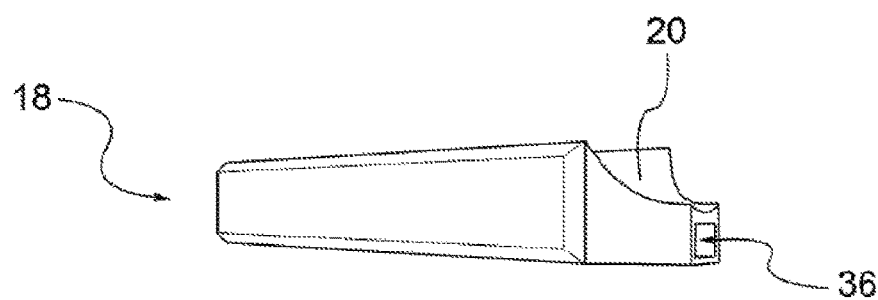

With reference to the above tables, by the reference number 1 has been indicated, in its totality, an assembly comprising a guide-wire 2 and a guide-wire kit 10 as detailed below.

The guide-wire 2 extends along a main direction X between a portion of proximal extremity and a portion of distal extremity, and distally comprises a flexible tip 4. Such tip is advantageously flexible to avoid damaging the vessels.

Within the present description, by the word "proximal" shall be meant the parts positioned or turned towards a guide-wire container 34 of the assembly, i.e., towards whosoever handles the assembly and the kit (more specifically, the medical staff performing the surgical operation); on the contrary, by the word "distal" shall be meant the parts or the directions facing or turned in the opposite direction, towards the flexible tip 4, i.e., towards the patient undergoing the operation.

Furthermore, always as regards the terminology used in the present description, by the expression "main direction"

shall not be meant merely rectilinear directions, but also (and above all) arched or curvilinear directions, inasmuch as substantially in no case is the guide-wire introduced along a straight or linear course, but often through the bifurcations, the deviations and/or along the tortuous sections of the blood vessels.

The guide-wire kit 10 comprises an introduction element 6 of the guide-wire 2 in an artery, which identifies an inner space 8 occupied by the guide-wire 2 and which is tapered in a distal direction—in accordance with the meaning discussed earlier—to create an opening through an introduction catheter, and in particular through a haemostatic valve of such catheter.

In fact, the guide-wire kit is configured to cooperate with an introduction catheter (not shown) inserted in the patient, proximally equipped with the haemostatic valve, so as to allow on the one hand the introduction of the guide-wire and other instruments into the artery, but on the other to prevent reverse-flow bleeding from the introduction catheter.

The introduction element 6 is therefore the instrument required to help the guide-wire surpass the haemostatic valve of the introduction catheter. When such valve is open and forced by the introduction element 6, a certain amount of reverse-flow bleeding is however possible from the introduction catheter which could potentially dirty the operating field.

Consequently, the portion of distal extremity 6' of the introduction element 6 is thinned (e.g., in a tubular way as shown, or in a truncated cone way) to wedge into the aforementioned valve, and this way permits the access of the guide-wire into the patient through the introduction catheter.

The introduction element 6 preferably has a substantially conical shape with the base of the cone turned in proximal direction, and delimits a proximal access opening 28 and a distal access opening 46 to the inner space 8. For example, the distal access opening 46 is positioned in correspondence to the thinned distal extremity portion 6'.

In agreement with a preferred embodiment, the proximal access opening 28 to the inner space 8 is at least partially closed by a haemostatic partition 30, configured to limit the escape of blood entering the inner space 8, and more specifically reverse-flow bleeding coming out of the haemostatic valve from the introduction catheter. Naturally, such partition is not essential to the main objects of the invention but provides a useful further advantage.

In particular, such partition can be fixed to a proximal extremity of the introduction element 6, e.g., in a removable way, so as to narrow the section of transit through the proximal access opening 28. In this respect, an embodiment can also foresee that a portion of the haemostatic partition 30 work on the outer surface of the guide-wire 2, so as to restrict its freedom of movement.

For the fixing and/or the removal of the haemostatic partition 30, this can be equipped with a grippable portion 48. For example, with reference to the variations shown, such portion 48 projects on the outside of a haemostatic partition 30 in the shape of a plate or cover.

In agreement with one variation, the assembly 1 can comprise a catheter or an instrument fitted in a sliding manner over a guide-wire 2, such catheter/instrument being specifically configured to perform an endoluminal procedure.

In other words, the described kit and the assembly can be separate entities to be joined to the catheter/instrument in the operating theatre during the medical procedure or, in agreement with the present variation, they can be made in a single specific assembly, e.g., disposable, to be used during determinate procedures by virtue of the catheter or of the premounted instrument.

The guide-wire kit also comprises a torque body 12, proximal to the introduction element 6, which delimits internally a longitudinal passage 14 to accommodate in part the guide-wire 2 (preferably in a roto-translatory manner), and which comprises blocking element 16 of the guide-wire 2 with respect to the torque body 12. Such means are switchable, in a reversible way, between a retention configuration wherein the blocking element 16 works on the guide-wire 2 to block it, and a release configuration to allow movements of the guide-wire 2 with respect to the above body 12.

Consequently, the blocking means act to fasten the guide-wire to the torque body, or to free it of such body, preferably narrowing or widening the transit section of the longitudinal passage.

In other words, the purpose of the blocking means is to block the guide-wire with respect to the torque body, and to transmit controlled torsion movements when the guide-wire shows high resistance to this movement, or when the operation requires high precision in the flexible tip.

For example, the torque body 12 comprises a generically tubular body wall 50 which identifies the longitudinal passage 14, such passage terminating at both extremities with a first 52 and a second 54 entrance opening. This way, the guide-wire engages such openings 52, 54 longitudinally crossing the torque body 12. Advantageously, the tubular body wall 50 extends around an axis parallel with or coincident to the main direction X of the guide-wire 2 in that section.

In agreement with an embodiment, the blocking element 16 comprise an insert 32 which engages the torque body 12 in a screwable manner. More specifically, such insert comprises an operating head 58, which can be operated by the user of the assembly/kit to command the switch between the above configurations, from which head extends a threaded stem 60 inserted in the torque body 12.

In this respect, the torque body 12 preferably identifies an insert housing 56, threaded in a complementary way to the threaded stem 60, which extends in a direction incident to the main direction X of the guide-wire 2, i.e., in a direction radial to this.

This way, in the retention configuration, a portion of the stem 60' of the insert 32 projects into the longitudinal passage 14 narrowing it, to make the guide-wire 2 integral with the above body 12.

The assembly can optionally envisage a guide-wire container 34, fixable proximally to the torque body 12 and/or to the slide control 18, in which it is accommodated and from which the guide wire 2 is gradually fed. Preferably, the guide-wire container can be released from the torque body 12 and/or from the slide control 18, and is preferably reconnectable to the one and/or the other.

In agreement with the embodiment shown in the FIG. 5, a distal section 62 of the guide-wire container 34 is at least partially inserted in the longitudinal passage 14, in particular through the first entrance opening 52.

In agreement with a particularly advantageous embodiment, the guide-wire container 34 is wound around itself in a plurality of concentric spirals 44', 44". For example, such container can comprise a tube wound in a spiral-shaped way, where the outermost spiral can be connected to the torque body, optionally as shown with respect to the preceding variations.

In agreement with a variation, the plurality of spirals 44', 44'' can furthermore be kept substantially planar by means of one or more radial bindings 64, 64' which join such spirals; the plurality of bindings is optionally angularly distance along the spirals.

The guide-wire kit also comprises a slide control 18 which delimits a support surface 20 for the guide-wire 2, manually accessible by the operator to control (roto)translations of the guide-wire 2, thereby orientations and/or sliding of the flexible tip 4, when the blocking element 16 are in the release configuration. Advantageously, the flexible tip 4 has a certain inclination compared to the main direction X, as schematized in the figures. Preferably, the support surface 20 is concave.

In fact, by making the guide-wire slide on the support surface 20 (e.g., using a finger, and in particular by causing a sliding on such surface using the thumb of one hand), the user of the assembly is able to force the flexible tip 4 to perform desired movements, in particular to make it move forward/reverse along the main direction X, or make it rotate with desired angles around a rotation axis parallel with such direction X. This way, the guide-wire can be commanded by the kit 10 to insert itself in specific branch vessels, and reach the anatomical area of the patient on which surgical intervention is required.

In other words, the flexible tip 4 of the guide-wire 2 is purposely curved to make engagements in the bifurcations easier, but very often there is a resistance to this movement and an instrument has to be applied which permits an improved manipulation of the guide-wire. In this respect, the torque body is provided.

Consequently, when we desire to enter a specific branch, the procedure requires an attempt to engage the ostium of a vessel by adequately rotating the guide-wire exploiting the curvature or the sinuosity of the flexible tip. Such operation can be performed using only the user's fingers, but in some circumstances it can turn out shoddy or even impossible due to the high resistance produced by the friction of the guide-wire itself.

In agreement with an embodiment (not shown), the guide-wire container 34 is fixable proximally to the slide control 18, which preferably proximally shows a specific engagement seat for such container. Preferably, such fastening is releasable.

This way, when the use of the torque body is not necessary during one of the operating phases, such body can be removed from the guide-wire and the guide-wire container 34 can be fitted directly to the slide control 18 to manually pilot, and in larger space conditions, torsions and/or translations of the guide-wire. According to this embodiment it could be advantageous for the body which realizes the slide control 18 to be of small enough dimensions to be grippable.

In agreement with a particularly advantageous variation, the torque body 12, the introduction element 6 and the slide control 18 are connected together in a releasable way.

In other words, such components can be used singularly as a monobloc, or can be split so as to make use of them singularly. By way of example only, the introduction element 6 be left in a certain position, e.g., engaged with the haemostatic valve, while the components proximal to it can be moved away to create work space or to be more conveniently operated.

In agreement with a further embodiment, the introduction and the slide control can be realized in reciprocal pieces, but in this variation it is preferable that such components can be disjointed, e.g., breaking or tearing the part that joins them together.

In agreement with the shown variation, the torque body 12, the introduction element 6 and the slide control 18 are of connectable shape. A further embodiment can envisage a reciprocal forced coupling.

Preferably, the slide control 18 is in part projecting from the torque body 12 in distal direction (and, consequently, is partially or prevalently accommodated in the torque body 12) and, even more preferably, such slide is placed between the introduction element 6 and the torque body 12.

With regard to such embodiment, it is a good idea for the space or the distance between the introduction element 6 and the torque body 12 to be large enough to allow one of the user's fingers or thumbs to enter it, and the subsequent sliding of such anatomic part on the support surface 20.

In agreement with an embodiment, in the retention configuration, the blocking element 16 acts (optionally the portion of stem 60' acts) radially on the guide-wire 2 to stop it precisely against the support surface 20 of the slide control 18.

According to an advantageous variation, the introduction element 6 can comprise a proximal connection arm 26 configured to be joined to a housing 36 of the slide control 18, preferably so as to create with it a prismatic pair. It follows that the introduction element 6 and the slide control 18 are connected together by means of a coupling of prismatic type, in a fast way.

In agreement with a further variation (not shown), such configuration can be reversed, in particular by obtaining a hollow housing in the introduction element, and making a connection arm on the slide control.

For the variations envisaging a connection arm (proximal), the haemostatic partition 30 can be shaped to couple itself in terms of shape with such arm. For example, the above partition can delimit a coupling recess 42 with the arm, so as to fork the latter. Advantageously, the coupling recess lies in a position opposite the partition 30 with respect to the grippable portion 48 (where provided).

In agreement with some of the previously shown embodiments, an edge of the coupling recess 42 preferably works on the outer surface of the guide-wire 2 to restrict its freedom of movement (e.g., the sliding), and specifically cooperating with the connection arm According to a further embodiment, in the inner space 8 of the introduction element 6 is obtained a slide section 38 which delimits a supporting surface 40 for the guide-wire 2 which realizes a distal extension of the slide control 18. This section can extend in a way correspondingly concave to the support surface 20.

Furthermore, the torque body 12, the introduction element 6 and the slide control 18 are each disengageable from the guide-wire 2, independently from the others, in a radial direction.

In other words, in order to separate the above mentioned components from the guide-wire, their laborious axial disjointing is not necessary—more specifically making them reverse as far as the proximal end of the guide-wire or, on the contrary, removing these from the distal extremity of this after having fully extracted it from the artery—but they simply have to be moved away from the guide-wire in a radial direction.

In agreement with a first embodiment, a wall 66 of the introduction element 6, which delimits the inner space 8, has a weakening line 68 tearable to detach the guide-wire 2 from the element 6 in the radial direction. For example, such line can comprise a thinning of the wall 66, such as a longitudinal V-shaped recess, which extends in particular between the proximal access opening 28 and the distal access opening 46.

According to a further embodiment, the wall 66 of the introduction element 6 (or the introduction element itself) are at least partially made of a transparent material, e.g., in order to visually establish whether the flexible tip 4 has distally surpassed the introduction element 6, or whether such tip has surpassed the haemostatic valve of the introduction catheter.

In agreement with a further embodiment, the torque body 12 delimits a body longitudinal groove 22, through which the longitudinal passage 14 is radially accessible for the guide-wire 2. It follows that, when the guide-wire 2 occupies the longitudinal passage 14, it can be made to come out of the torque body 12 making it transit radially from the body longitudinal groove 22.

Figure 9A:
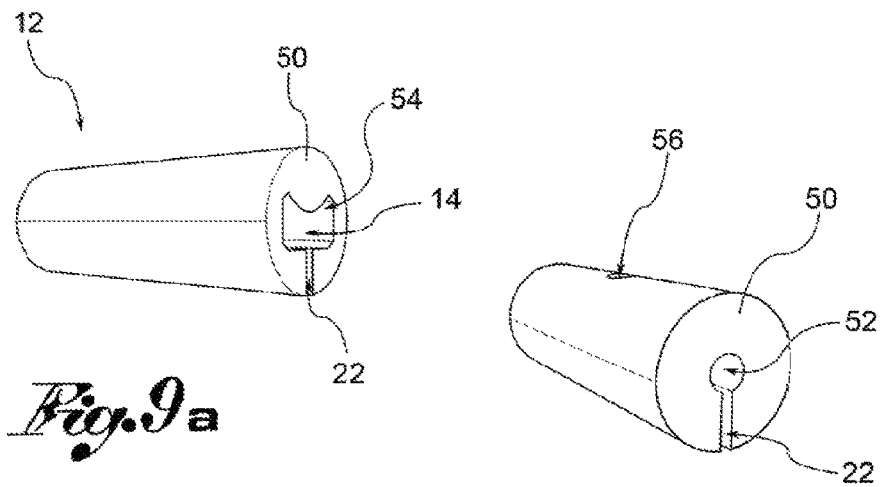
Figure 9B:
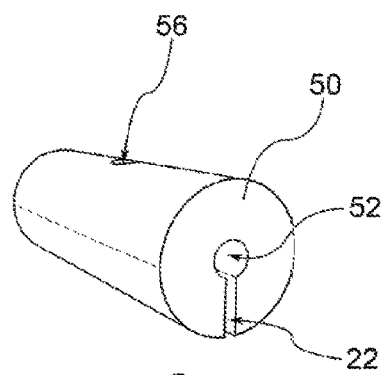

In agreement with the embodiment shown in the FIG. 9*b*, the insert seat 56 and the body longitudinal groove 22 lie diametrically opposite.

According to a still further variation, the torque body 12 delimits a slide seat 24 in which the slide control 18 is partially or prevalently accommodated, e.g., with a shaped coupling. Advantageously, the slide seat 24 is realized by a portion (distal) of the longitudinal passage 14, which can specifically have a variation or an increase in section to allow the housing of the slide control 18. Preferably, the torque body 12 and the slide control 18 make a prismatic pair. For example, the slide seat 24 can be conformed so as to accommodate the slide in translation, but prevent its rotations parallel with the direction of translation.

According to a particularly preferred embodiment, the slide control 18 overlaps for at least a section the longitudinal groove of the body 22 to retain the guide-wire 2 in the torque body 12, and is advantageously accommodated in the torque body 12 and/or in the slide seat 24 in a removable way.

In other words, according to the different embodiments expounded previously, slide control performs a plurality of functions inasmuch as it is the component which can be used singularly with the guide-wire to command the discussed movements of the flexible tip, inasmuch as it prevents the disengagement of the guide-wire from the longitudinal passage 14 (as long as it is inserted in the torque body 12), by virtue of the fact that it is the part of the assembly 1 which acts as locator for the retention action of the blocking element 16, and/or creates a joint between the introduction element 6 and the torque body 12.

A further object of the present invention is a method for using a guide-wire assembly 1, e.g., according to any one of the preceding embodiments, preferably, but not only, outside the human body.

Such method of use comprises the following phases:
  providing a guide-wire 2, which extends along a main direction X and which distally comprises a flexible tip 4;
  providing an introduction element 6 of the guide-wire kit 10, which identifies an inner space 8 and which is tapered in a distal direction;
  inserting the guide-wire 2 in the inner space 8 of the introduction element 6;
  providing a slide control 18 of the guide-wire kit 10, which delimits a support surface 20 for the guide-wire 2;
  manually controlling (roto-)translations of the guide-wire 2, thereby orientations and/or sliding of the flexible tip 4, working with a finger/thumb on the support surface 20 and on the guide-wire 2;
  disengaging the introduction element 6 and/or the slide control 18 from the guide-wire 2 in a radial direction.

Besides the method phases directly or indirectly deductable from the preceding description, into which we shall not delve again here, preferred embodiments of the present method comprise the following further phases:
  providing a torque body 12 of the guide-wire kit 10, which internally delimits a longitudinal passage 14 and which comprises blocking element 16 of said guide-wire 2 with respect to said body 12, such means being reversibly switchable;
  accommodating in part the guide-wire 2 in the longitudinal passage 14 in a radial direction;
  proximally to the introduction element 6, connecting the torque body 12 to the slide control 18, e.g., with a shaped coupling, so that such slide 18 projects in part from the torque body 12 in distal direction; and
  optionally disengaging the torque body 12 from the guide-wire 2 in a radial direction.

In other words, preferred embodiments of use of the above assembly provide for the torque body to be part of the kit (e.g., as sterile assembly), but that it only be used in case of need, always connecting it in a radial direction of the guide-wire to overcome the drawbacks tied to the prior art. For example, the torque body can be used to transmit controlled torsion movements when the guide-wire shows high resistance to this movement, or when the operation requires high precision in directing the flexible tip.

A further object of the present invention is a method for mounting a guide-wire assembly 1, e.g., according to any one of the previously-illustrated embodiments, comprising the following phases:
  providing an introduction element 6 of a guide-wire 2 in an artery, which identifies an inner space 8 and which is tapered in a distal direction to create an opening through an introduction catheter;
  providing a torque body 12, proximal to the introduction element 6, which internally delimits a longitudinal passage 14 and which comprises blocking element 16 of said guide-wire 2 with respect to said body 12, reversibly switchable between a retention configuration wherein said blocking element 16 work on the guide-wire 2 to block it, and a release configuration to permit movements of the guide-wire 2 with respect to said body 12;
  providing a slide control 18 which delimits a support surface 20 for the guide-wire 2, manually accessible to control (roto-)translations of the guide-wire 2, thereby orientations and/or sliding of the flexible tip 4, when said blocking element 16 are in the release configuration;
  connecting together the torque body 12, the introduction element 6 and the slide control 18.

Optionally, such mounting method comprises a phase of accommodating, partially or prevalently, the slide control 18 in a slide seat 24 of the torque body 12 to retain the guide-wire 2 in the torque body 12.

According to still further embodiments of the mounting method, the following phases are also envisaged:
  providing the guide-wire 2, which extends along a main direction X and which distally comprises a flexible tip 4, wherein the guide-wire 2 is accommodated and gradually fed by a guide-wire container 34;
  optionally allowing the guide-wire 2 to transit in the inner space 8 of the introduction element 6, in the longitudinal passage 14 of the torque body and on the support surface 20 of the slide control 18;

fixing the guide-wire container 34 proximally to the torque body 12 and/or to the slide control 18.

Innovatively, the assembly and the kit forming the subject of the present allow easily freeing the area of entrance of the instruments in the patient in a simple and reversible way, in particular without the structures needed to position the guide-wire having to be made to come out axially from such wire. In fact, the described assembly and kit are configured to allow the rapid dismantling of the above structures, and an equally rapid reconnection to the guide-wire in case of renewed need.

Furthermore, the medical staff using the kit or the assembly can even freely decide which components have to be maintained for the operation and which instead have to be retaken after a period of time, precisely by virtue of the connectivity that distinguishes the present invention.

Advantageously, the assembly forming the subject of the present invention can be fabricated as a sterile pre-packed instrument, with the guide wire already available for use, so as to considerably speed up the preparatory phases for a surgical operation.

Furthermore, advantageously, the assembly forming the subject of the present invention can be fabricated in a sterile way including with a determinate catheter or pre-loaded instrument; such advantage can be even more appreciated when very thin stents or lumen bags are manipulated, where the fitting of the guide-wire is less easy for not only dimensional reasons.

In fact, in some cases of very fine catheters, where the fitting of the guide to the catheter is difficult, the guide-wire can be offered by a manufacturer already fitted on the catheter without preventing the possibility of using the introduction element and/or the torque body.

Advantageously, by virtue of the previously-described preparation, the operating area can be kept very tidy during any phase of the operation, inasmuch as the guides can be left at length in the space belonging to them, and optionally can be made to return there in case of need.

Advantageously, the assembly and the kit forming the subject of the present invention permit more controlled operations by the medical staff, because the different components and the material to be manipulated always remain confined inside a very small space.

Advantageously, the assembly and the kit forming the subject of the present invention are configured for the insertion of even very fine bags in the patient, which have no difficulty in distally transiting beyond the introduction element.

Advantageously, the shape of the previously-described components is extremely ergonomic and so it permits detaching or joining the parts back together, to grip the system firmly and to control with millimetric precision the orientation and/or the translation of the flexible tip. This way, the guide-wire can be kept in determinate positions, and specific anatomic areas can be prevented from being accidentally hit during guide-wire maneuver.

Advantageously, in some circumstances, the assembly and the kit forming the subject of the present invention permit extracting an instrument just outside the introduction element, and applying a torsion on the guide-wire without such instrument having to be completely removed from the guide wire.

In other words, the assembly and the kit forming the subject of the present invention make possible the easy manipulation of the guide-wire without the other instruments used having to be completely separated from the guide.

Advantageously, the intensity of retention of the guide-wire by the torque body is adjustable, so as to be able to change the easiness of torsion or forward movement of the guide-wire according to requirements.

Advantageously, the assembly and the kit forming the subject of the present invention permit limiting pointless patient blood loss, not always negligible, but often troublesome inasmuch as it covers with fibrin and coagulated blood the other instruments used during the surgical operation.

To the embodiments of the above assembly and kit, a technician in the field, in order to satisfy specific requirements, could make changes to or replace the elements with others which are functionally equivalent.

Such variations are also included within the scope of protection as defined by the following claims.

Furthermore, each variation described as belonging to a possible embodiment can be made independently from the other described variations.

The invention claimed is:

1. Assembly for inserting a guide-wire; having a flexible tip in order to insert an introduction catheter into a patient's vessel, the assembly comprising:
   i) an introduction element, having an inner space occupied by the guide-wire, the introduction element being tapered in a distal direction to create an opening through the introduction catheter;
   ii) a torque body, proximal to the introduction element, which delimits internally a longitudinal passage to receive in part the guide-wire, the torque body having a blocking device comprising an insert extending through a wall of the torque body, the insert-configured for being reversibly switched between a retention configuration when advanced against the guide wire, and a release configuration, when in disengagement from the guide wire, to permit movements of the guide-wire in relation to said torque body; and,
   iii) a slide control proximal to the introduction element, and capable of being slidably positioned within the torque body, the slide control having a support surface for the guide-wire thereby allowing orientations and/or sliding of the flexible tip, when said blocking device is in the release configuration;

said assembly being characterized in that the torque body, the introduction element and the slide control are each disengageable, independently of the others, from the guide-wire in a radial direction.

2. Assembly according to claim 1, wherein the torque body, the introduction element and the slide control are removably connected to each other.

3. Assembly according to claim 2, wherein the torque body and the slide control are connected to each other in a releasable manner, and wherein the introduction element and the slide control are connected to each other in a releasable manner.

4. Assembly according to claim 1, wherein the slide control is positioned between the introduction element and the torque body, said slide control projecting in part from the torque body in a distal direction.

5. Assembly according to claim 1, wherein the torque body delimits a longitudinal body groove, through which the longitudinal passage for the guide-wire is radially accessible, and, wherein the torque body optionally delimits a slide seat in which the slide control is at least partially extractably housed, said slide control overlapping at least a section of the longitudinal body groove to retain the guide-wire in the torque body.

6. Assembly according to claim 1, wherein, in the retention configuration, the blocking device is capable of being advanced to act radially on the guide-wire to block the guide wire against the support surface of the slide control.

7. Assembly according to claim 1, wherein, in the inner space of the introduction element, is obtained a slide section, which forms a distal extension of the slide control and which defines a supporting surface for the guide-wire.

8. Assembly according to claim 1, wherein the introduction element comprises a housing or a proximal connection arm configured to be joined to a projection or to a housing of the slide control so as to make a prismatic pair therewith.

9. Assembly according to claim 1, wherein a proximal access aperture of the inner space is at least partially closed by a haemostatic partition, configured to limit blood exiting or entering the inner space.

10. Assembly according to claim 1, wherein the insert includes a threaded surface for engagement with the wall of the torque body in a screwable manner, so that in the retention configuration a stem portion of said insert projects into the longitudinal passage to make the guide-wire integral with said body.

11. Assembly according to claim 1, wherein the assembly further includes a guide-wire container, which receives the guide wire and from which the guide-wire is progressively fed, proximally attached to the torque body and/or to the slide control.

12. Assembly according to claim 1, wherein the assembly further includes a catheter or an instrument fitted in a sliding manner onto the guide-wire, said catheter/instrument being specifically configured to perform an endoluminal procedure.

13. Assembly according to claim 1, wherein a wall of the introduction element has a weakening line, tearable to detach the guide-wire from said element in the radial direction.

* * * * *